United States Patent [19]

Ollinger

[11] Patent Number: 4,468,389

[45] Date of Patent: Aug. 28, 1984

[54] PESTICIDAL N-SULFONYL PHOSPHORODIAMIDO(DI)THIOATES

[75] Inventor: Janet Ollinger, Chalfont, Pa.

[73] Assignee: Rohm and Haas Company, Philadelphia, Pa.

[21] Appl. No.: 380,576

[22] Filed: May 21, 1982

[51] Int. Cl.$^3$ .................. A01N 57/28; C07F 9/24
[52] U.S. Cl. .................. 424/215; 260/940; 260/941; 260/943; 260/944; 260/947; 424/211
[58] Field of Search .............. 260/943, 947, 940, 941, 260/944; 424/211, 215

[56] References Cited

U.S. PATENT DOCUMENTS

| | | | |
|---|---|---|---|
| 3,657,426 | 4/1972 | Schroeder | 424/200 |
| 3,716,600 | 2/1973 | Magee | 260/950 |
| 3,810,959 | 5/1974 | Gaughan | 260/941 |
| 3,887,657 | 6/1975 | Battershell et al. | 260/938 |
| 3,898,260 | 8/1975 | Meyer et al. | 260/455 P |
| 3,917,845 | 11/1975 | Brown | 424/215 |
| 3,957,924 | 5/1976 | Meyer et al. | 260/938 |
| 4,056,581 | 11/1977 | Bayer et al. | 260/972 |
| 4,161,524 | 7/1979 | Kishino et al. | 424/215 |
| 4,263,288 | 4/1981 | Ollinger | 424/210 |
| 4,279,897 | 7/1981 | Fahmy et al. | 424/211 |
| 4,315,870 | 2/1982 | Ollinger | 260/947 |

FOREIGN PATENT DOCUMENTS

| | | |
|---|---|---|
| 113551 | 6/1975 | German Democratic Rep. . |
| 2128325 | 4/1976 | Japan . |
| 464592 | 3/1975 | U.S.S.R. . |

*Primary Examiner*—Anton H. Sutto

[57] ABSTRACT

There are disclosed N-sulfonyl phosphorodiamido(di)-thioates having pesticidal activity, especially miticidal activity against mites possessing resistance to organophosphorous compounds, when applied to pests or to loci to be freed from the pests by foliar or systematic application techniques.

16 Claims, No Drawings

PESTICIDAL N-SULFONYL PHOSPHORODIAMIDO(DI)THIOATES

BACKGROUND OF THE INVENTION

1. Field of the Invention

This invention relates to novel N-sulfonyl phosphorodiamido(di)thioate compounds, to compositions thereof which are useful are pesticides, more specifically as acaricides, insecticides, and nematocides, and to a method of controlling pests in agricultural plants. These compounds also exhibit fungicidal activity.

2. Description of the Prior Art

Ollinger, U.S. Pat. No. 4,315,870 issued Feb. 16, 1982 discloses acaricidal, insecticidal and nematicidal phosphorodiamidothioates represented by the formula

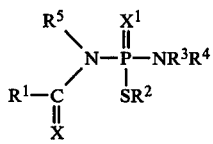

wherein $R^1$, $R^2$, $R^3$, $R^4$, and $R^5$ are selected from unsubstituted and substituted alkyl, alkenyl, alkynyl, phenyl, and phenylalkyl groups and X and $X^1$ are selected from oxygen and sulfur atoms.

Magee, U.S. Pat. No. 3,716,600, discloses insecticidal phosphoroamidothioates represented by the formula

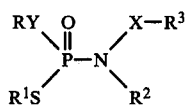

wherein R is $C_1$–$C_3$ alkyl; $R^1$ is $C_1$–$C_3$ alkyl, alkenyl or alkynyl; $R^2$ is hydrogen or $C_1$–$C_3$ alkyl; X is carbonyl or sulfonyl; and Y is oxygen or sulfur; when X is sulfonyl, $R^3$ is $C_1$–$C_{10}$ alkyl, $C_3$–$C_8$ cycloalkyl or phenyl; and when X is carbonyl, $R^3$ is hydrogen, $C_1$–$C_{18}$ containing 1-4 halogens selected from F and Cl and Br, $C_2$–$C_{18}$ alkenyl, $C_3$–$C_{18}$ alkynyl, a heterocyclic radical of 1 hetero oxygen, sulfur, or nitrogen atom and 4 or 5 annual C atoms and a total of 4 to 8 carbon atoms, $C_2$–$C_{12}$ alkoxyalkyl, $C_2$–$C_{12}$ alkylthioalkyl, $C_1$–$C_{12}$ alkoxy, $C_1$–$C_{12}$ alkylthio, pheny, phenyl substituted with 1 or 2 $C_1$–$C_3$ alkyl radicals or $C_1$–$C_3$ alkoxy radicals or halogen atoms selected from F and Cl and Br or $NO_2$ groups, styryl, phenyl ($C_1$–$C_3$) alkyl, phenoxy ($C_1$–$C_3$) alkyl, thiophenoxy ($C_1$–$C_3$) alkyl, or phenoxy ($C_1$–$C_3$) alkyl or thiophenoxy ($C_1$–$C_3$) alkyl in which the aromatic moiety is substituted with halogens selected from F and Cl and Br or mono-nitro ($C_1$–$C_3$) alkyl.

Kishino et al., U.S. Pat. Nos. 4,134,979 (Jan. 16, 1979) and 4,161,524 (July 17, 1979), disclose insecticidal, acaricidal and nematicidal O-alkyl-S-n-propyl-N-sulfonyl-phosphoric acid ester amides represented by the formula

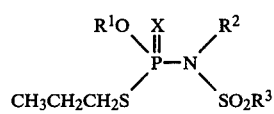

wherein $R^1$ is methyl or ethyl; $R^2$ is unsubstituted $C_1$–$C_6$ alkyl or alkenyl, or $C_1$–$C_6$ alkyl substituted by aryl, phenyl, $C_1$–$C_6$ alkylphenyl, or halophenyl; $R^3$ is $C_1$–$C_6$ alkylphenyl, $C_1$–$C_6$ alkoxyphenyl, halophenyl, or nitrophenyl; and X is O or S.

Japanese Patent No. 5 2,128,325 (Derwent Abstract 87 421 Y/49) discloses insecticidal, nematocidal and miticidal organic phosphoric acid amide esters represented by the formula

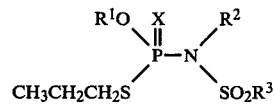

wherein $R^1$ is methyl or ethyl; $R^2$ is lower alkyl, alkenyl, aralkyl or phenyl substituted with up to three alkyl or halogen groups; $R^3$ is lower alkyl, haloalkyl or phenylalkyl wherein the phenyl ring may be substituted with up to three substituents selected from lower alkyl, nitro or lower alkoxy; and X is O or S.

DESCRIPTION OF THE INVENTION

It is an object of the invention to provide compounds, and compositions thereof, which possess pesticidal, such as insecticidal, acaricidal, nematocidal and miticidal activity, and which are especially active against mites possessing resistance to organo-phosphorous compounds.

It is another object of the invention to provide a method of controlling pests, namely insects, acarids, mites and nematodes.

These and other objects as will become apparent are achieved by the present invention which comprises compounds having the formula wherein

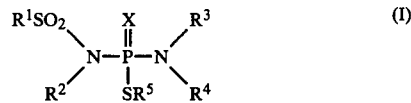

(I)

$R^1$ is unsubstituted or substituted $C_1$–$C_6$ alkyl wherein the substituent can be from one to three of the same or different halogens selected from Cl, Br, or F groups;

$C_3$–$C_8$ cycloalkyl;

unsubstituted or substituted phenyl or naphthyl, or can be one to three of the same or different substituents selected from cyano, nitro, halo, alkyl, alkoxy, alkylthio, alkylsulfinyl, alkylsulfonyl, phenoxy, haloalkyl, mono- or di-alkylamino, mono- or di-alkylaminocarbonyl, alkoxy-carbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenyloxycarbonyl, alkenylcarbonyloxy, aminocarbonyl, or alkylcarbonylamino and the like wherein the alkyl moiety thereof is a straight or branched chain group containing one to six carbon atoms;

$R^2$ is hydrogen;

unsubstituted or substituted $C_1$–$C_6$ alkyl wherein the substituent can be a halo, cyano, alkoxy, alkylthio, alkylcarbonyl, alkoxycarbonyl, alkoxycarbonyloxy, mono- or di-alkylamino, phenoxy or phenylthio groups;

$C_3$–$C_8$ cycloalkyl;

$C_3$–$C_6$ alkenyl;

unsubstituted or substituted phenyl or naphthyl, or unsubstituted or substituted phenyl($C_1$–$C_5$)alkyl, wherein the substituent on the phenyl or naphthyl ring can be one to three of the same or different substituents selected from cyano, nitro, halo, alkyl, alkoxy, alkylthio, alkylsulfinyl, alkylsulfonyl, phenoxy, haloalkyl, mono- or di-alkylamino, mono- or di-alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxyl, phenylaminocarbonyl, alkenyloxycarbonyl, alkenylcabonyloxy, aminocarbonyl, or alkylcarbonylamino and the like wherein the alkyl moiety thereof is a straight or branched chain group containing one to six carbon atoms;

$C_3$–$C_6$ alkynyl;

$R^3$ is hydrogen, methyl or ethyl;

$R^4$ is hydrogen, methyl, $C_1$–$C_6$ alkylthio($C_1$–$C_2$)alkyl, $C_1$–$C_6$ alkoxy($C_1$–$C_2$)alkyl, $C_3$–$C_4$ alkenyl, $C_3$–$C_4$ alkynyl;

$R^5$ is $C_2$–$C_6$ alkyl; and

X is O or S, preferably O.

More preferred are those compounds of formula I wherein $R^1$ is an unsubstituted or substituted $C_1$–$C_6$ alkyl group wherein the substituent can be from one to three of the same or different halogens selected from chloro, bromo or fluoro groups;

$R^2$ is an unsubstituted or substituted $C_1$–$C_6$ alkyl group wherein the substituent can be a cyano, alkoxy, alkylthio, alkylcarbonyl, alkoxycarbonyl, alkylcarbonyloxy, mono- or di-alkylamino, phenoxy or phenylthio group;

a $C_3$–$C_6$ alkenyl group; or a $C_3$–$C_6$ alkynyl group;

$R^3$ is a methyl group;

$R^4$ is hydrogen, methyl, $C_3$–$C_4$ alkenyl; $C_3$–$C_4$ alkynyl;

$R^5$ is $C_2$–$C_6$ alkyl; and

X is O.

These compounds are more preferred because they provide advantageous pesticidal efficacy.

Most preferred are those compounds of formula I wherein $R^1$ is an unsubstituted or substituted $C_1$–$C_6$ alkyl group wherein the substituent can be one to three of the same or different halogens selected from chloro, bromo or fluoro groups;

$R^2$ is an unsubstituted $C_1$–$C_3$ alkyl group;

a $C_3$-alkenyl group; or a $C_3$-alkynyl group;

$R^3$ is methyl;

$R^4$ is hydrogen;

$R^5$ is 1-methylpropyl; and

X is O.

These compounds are most preferred because they provide especially advantageous pesticidal efficacy.

In another aspect, the invention comprises a pesticidal composition comprising a pesticidally effective amount of the compound of formula I and an agronomically acceptable carrier.

In yet another aspect, the invention comprises a method of controlling pests comprising applying to the pests or to the loci of plants to be freed from infestation by the pests a pesticidally effective amount of the compound of formula 1.

As used in the specification and claims, the terms "alkyl", "alkenyl", and "alkynyl" are meant to include both branched and straight chain alkyl, alkenyl, and alkynyl groups. Representative examples of such groups include methyl, ethyl, propyl, isopropyl, sec-butyl, isobutyl, tert-butyl, pentyl, neopentyl, hexyl, allyl, 2-butenyl, 3-methyl-1-pentenyl, 3-hexenyl, propynyl, 1-pentynyl, 4-methyl-1-pentynyl, hexynyl, and the like.

By "alkenyl" group, as used in the specification and the claims, is meant an alkenyl group such as an allyl group, or the like, with one cis or trans double bond.

By "alkynyl" group, as used in the specification and the claims, is meant an alkynyl group, such as a propargyl group, with one triple bond.

By a substituted phenyl($C_1$–$C_5$)alkyl group is meant a phenyl($C_1$–$C_5$)alkyl group, e.g., benzyl, phenethyl, 3-phenyl-1-methylpropyl, etc., the phenyl ring of which is substituted with one or more, but preferably with one to three substituents selected from the group of substituents defined for substituted phenyl above.

Representative compounds of the invention include those compounds listed below:

N-Methanesulfonyl N,N'-dimethyl S-pentyl phosphorodiamidothioate

S-Ethyl N-hexanesulfonyl N-hexyl phosphorodiamidothioate

N-Cyclopropanesulfonyl N-(2-methoxyphenyl) N'-methyl S-propyl phosphorodiamidothioate N-(4-Bromophenyl) N-cyclohexanesulfonyl N'-ethyl S-hexyl phosphorodiamidothioate N'-Methyl S-pentyl N-phenylsulfonyl N-phenyl phosphorodiamidothioate N-(4-Chlorophenyl)sulfonyl N-cyclopropyl S-ethyl N'-(2-propenyl) phosphorodiamidothioate N-Benzylsulfonyl N-cyclohexyl N'-(2-propynyl) S-propyl phosphorodiamidothioate N-(4-Bromobenzyl)sulfonyl N-methyl S-pentyl N'-(2-propenyl) phosphorodiamidothioate N-Cyanoethyl N'-ethyl N-phenylsulfonyl S-propyl phosphorodiamidothioate N-(1-Ethoxyhexyl) N'-methyl N-(4-nitrophenylsulfonyl) S-pentyl phosphorodiamidothioate N'-Methyl S-(1-methylpropyl) N-(2-methylthioethyl) N-trifluoromethanesulfonyl phosphorodiamidothiaote N-(3-Chlorohexyl)sulfonyl N-(2-methoxycarbonyl)-hexyl N'-methyl S-(1-methylpropyl) phosphorodiamidothioate N-(Ethoxycarbonyl)methyl N'-ethyl S-propyl N-trichloromethanesulfonyl phosphorodiamidothioate N-(4-Bromohexane)sulfonyl N'-methyl S-(1-methylpropyl) N-(4-phenoxyhexyl) phosphorodiamidothioate S-Butyl N-(3-hexynyl) N'-methyl N-trichloromethanesulfonyl phosphorodiamidothioate S-(1-Methylethyl) N-(2-propynyl) N'-methyl N-trifluoromethanesulfonyl phosphorodiamidothioate N-(2-Hexenyl) N'-methyl S-(1-methylpropyl) N-trifluoromethanesulfonyl phosphorodiamidothioate N-(3-Chloropropyl)sulfonyl N-hexyl S-(2-methylpropyl) N'-(2-propenyl) phosphorodiamidothioate N-(3-Chloropropyl)sulfonyl N,N'-dimethyl S-propyl phosphorodiamidothioate N-Methanesulfonyl N,N'-dimethyl S-(1-methylpropyl) phosphorodiamidodithioate S-Butyl N-hexanesulfonyl N-(2-methoxyethyl) N'-methyl phosphorodiamidodithioate N-Cyclopropanesulfonyl N,N'-dimethyl S-hexyl phosphorodiamidothioate N-(4-Bromophenylsulfonyl) N-ethyl S-propyl phosphorodiamidodithioate N'-Methyl S-(2-methylpropyl) N-(2-methylthioethyl) N-trifluoromethanesulfonyl phosphorodiamidodithioate N'-Ethyl N-(2-propenyl) S-propyl N-trichloromethylsulfonyl phosphorodiamidothioate S-(1-Methylpropyl) N-phenylsulfonyl N-(2-propynyl) phosphorodiamidodithioate N-Butanesulfonyl N-(3-hexynyl) S-(2-methylpropyl) N'-(2-propenyl) phosphorodiamidodithioate N-Ethyl N-ethanesulfonyl N'-methyl S-(2-methylpropyl) phosphorodiamidodithioate N-Butyl N-butanesulfonyl N',S-diethyl phosphorodiamidodithioate N-Butanesulfonyl N-(6-cyanohexyl) N'-methyl S-(1-methylethyl) phosphorodiamidodithioate N-(3-Methylpentyl) N-phenylsulfonyl N'-(2-propynyl) S-propyl phosphorodiamidothioate N-(3-Methylethyl)sulfonyl N-(2-methylpropyl) S-pentyl N-(2-propenyl) phosphorodiamidodithioate N-(2-Ethoxyethyl) N-(2-ethylbutanesulfonyl) N'-methyl S-(1-methylpropyl) phosphorodiamidodithioate.

Especially preferred embodiments embraced by the invention are:

N-methanesulfonyl N,N'-dimethyl S-(1-methylpropyl) phosphorodiamidothioate

N,N'-dimethyl N-(4-methylphenylsulfonyl) S-(1-methylpropyl) phosphorodiamidothioate N-methanesulfonyl N,N'-dimethyl S-(1-methylpropyl) N'-(2-propenyl) phosphorodiamidothioate N-ethyl N-methanesulfonyl N'-methyl S-(1-methylpropyl) N'-(2-propenyl) phosphorodiamidothioate N-methanesulfonyl N'-methyl S-(1-methylpropyl) N-methylthioethyl phosphorodiamidothioate N-methanesulfonyl N'-methyl S-(1-methylpropyl) N-(2-propynyl) phosphorodiamidothioate N,N'-dimethyl S-(1-methylpropyl) N-trifluoromethanesulfonyl phosphorodiamidothioate N-butanesulfonyl N,N'-dimethyl S-(1-methylpropyl) phosphorodiamidothioate The compounds of the invention can be synthesized, as is outlined in the sequence of reaction equations below, by reaction, carried out generally in the presence of an inert solvent, such as tetrahydrofuran (THF), chlorinated hydrocarbons, aromatic hydrocarbons, and ethers, at room temperature and atmospheric pressure, of a phosphorodichloridothioate (3) with a sodium salt of a sulfonamide (2) to form monochloride (4). Reaction, carried out generally in the presence of an inert solvent such as THF at room temperature and atmospheric pressure, of (4) with an amine in the presence of an acid scavenger, for example, excess amine, yields diamidate (I). The sodium salt (2) is formed by reaction, carried out generally in the presence of an inert solvent such as THF at room temperature and atmospheric pressure, of a sulfonamide (1) with a strong base, for example, sodium hydride or sodium hydroxide.

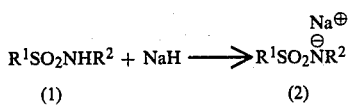

(1)  (2)

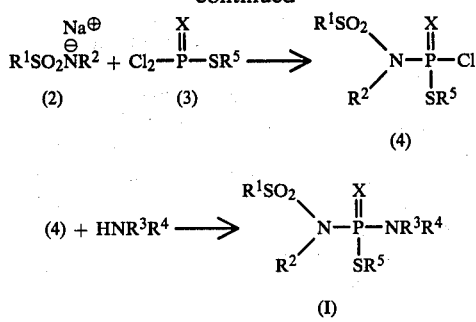

The preparation of phosphorodichloridothioates such as compound (3) above is described in Hurt, U.S. Pat. No. 4,056,581.

The compounds of the invention are useful for the protection of plants and animals, including mammals, from the ravages of harmful and annoying pests. These compounds are particularly effective against arthropods (in varying stages of development) and are especially effective against members of the Class Arachnoidea, which includes the Order Acarina, as represented by mites and ticks, and the Class Insecta, the insects. Among the arthropods which are effectively controlled by the compounds of the present invention are the chewing insects, e.g., the southern armyworm (*Spodoptera eridania*), mites, e.g., the two-spotted spider mite (*Tetranychus urticae*) and others.

The compounds of this invention are also active as fungicides.

Furthermore, compounds of this invention possess nematocidal activity. Among the nematodes which are effectively controlled by the compounds of the present invention are soil nematodes, typified by the southern root knot nematode (*Meloidogyne incognita*).

Generally, control of pests is achieved in accordance with this invention by application of the compounds in pesticidally effective amounts (e.g., arthropodicidally effective amounts) either directly to the pests to be controlled or to the loci to be freed of or protected from attack by such pests. Plant protection loci may be defined as the aerial and subterranean portions of plants or propagative subunits and their immediate or future environs. For example, food, fiber, forage, forest, and ornamental crops and stored products thereof represent plant protection loci. Treatment with compounds of this invention of domestic animals, and their immediate environs similarly constitute representative loci for protection against various annoying ectoparasitic or endoparasitic Acarina (Acari) and Insecta. Many of the formulations listed below can be utilized on animals in the control of parasites. Thus, the compounds can be deposited on or in the soil, plants, insects, manmade structures, or other substrates as deposits, coatings, etc. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, inhibition, reduction in number or any combination thereof.

The term "pest" as employed in the specification and claims of this application refers to fungi, nematodes and various arthropods especially insects and acarids.

The phosphorodiamidothioates of this invention possess general utility as arthropodicites, particularly as against members of the class Arachnoidea, which includes the order Acarina, as represented by mites and ticks, and Insecta, the insects. Certain compounds of this invention are also active as nematocides and fungicides, particularly fungicides.

For use as pesticides, the compounds of this invention can be used as solutions in organic solvents or formulations. For example, they can be formulated as wettable powders, emulsifiable concentrates, dusts, granular formulations or flowable emulsifiable concentrates. In such formulations, the phosphorodiamidothioates are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The phosphorodiamidothioates can be taken up or mixed with a finely particled solid carrier, as for example, clays, inorganic silicates, carbonates, and silicas. Organic carriers can also be employed. Dust concentrates are commonly made wherein phosphorodiamidothioates are present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or blend of these. The phosphorodiamidothioates are usually present in the range of about 10 to about 35% by weight and surfactants from about 0.5 to about 10% by weight.

One convenient method for preparing a solid formulation is to impregnate the phosphorodiamidothioate onto the solid carrier by means of a volatile solvent such as acetone. In this manner, adjuvants, such as activators, adhesives, plant nutrients, synergists and various surfactants can also be incorporated.

Emulsifiable concentrate formulations can be prepared by dissolving the phosphoramidothioates of this invention in an agronomically acceptable organic solvent and adding a solvent-soluble emulsifying agent. Suitable solvents are usually water-immiscible and can be found in the hydrocarbon, ketone, ester, alcohol and amide groups of organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 20 to about 50% by weight.

For use as pesticidal agents, these compounds should be applied in an effective amount sufficient to exert the desired pesticidal activity by techniques well known in the art. Usually, this will involve the application of the phosphorodiamidothioate to the loci to be protected from or freed of pests in an effective amount when incorporated in an agronomically acceptable carrier. However, in certain situations, it may be desirable and advantageous to apply the compounds directly onto the loci to be protected from or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purpose for such application, the phosphorodiamidothioate being utilized, the frequency of dissemination and the like.

By "agronomically acceptable carrier" is meant any substance which can be utilized to dissolve, disperse, or diffuse the chemical incorporated therein without impairing the effectiveness of the toxic agent and which does no permanent damage to such environment as soil, equipment and agronomic crops.

For use as insecticides and acaricides, dilute sprays can be applied at concentrations of about 0.01 to about 20 pounds of the phosphorodiamidothioate ingredient per 100 gallons of spray. They are usually applied at about 0.1 to about 5 pounds per 100 gallons. In more concentrated sprays, the active ingredient is increased by a factor of about 2 to about 12. With dilute sprays, applications are usually made to the plants until run off is achieved, whereas with more concentrated low-volume sprays, the materials are applied as mists.

For use as a fungicide, the compounds of this invention can be applied as fungicidal sprays by methods commonly employed, such as, conventional high-gallonage hydraulic sprays, low-gallonage sprays, air-blast sprays, aerial sprays and dusts. The dilution and rate of application will depend upon the type of equipment employed, the method of application and diseases to be controlled, but the preferred effective amount is usually about 0.1 lb. to about 50 lbs. per acre of the active ingredient.

As a fungicidal seed protectant, the amount of toxicant coated on the seed is usually at a dosage rate of about 0.1 to about 20 ounces per hundred pounds of seed. As a soil fungicide the chemical can be incorporated in the soil or applied to the surface usually at a rate of about 0.1 to about 50 lbs. per acre. As a foliar fungicide, the toxicant is usually applied to growing plants at a rate of about 0.25 to about 10 lbs. per acre.

For use as a nematocide, systemic agent, or as a soil insecticide, the phosphorodiamidothioates can be applied as a solid formulation, preferably a granular formulation or as a diluted liquid preparation, by broadcasting, sidedressing soil incorporation or seed treatment.

The composition can also be added to transplant or irrigation water or to units employed in propagation, such as, seeds, tubers, roots, seedlings, etc., so as to disinfect and/or provide residual protection from nematodes, soil insects (and mites) and via systemic uptake, foliar pests. The application rate can be from about 0.5 to about 50 pounds per acre; however, higher rates can also be used. The preferred rate is from about 1 to about 25 pounds per acre. For soil incorporation, the compounds of this invention can be mixed with the soil or other growth medium at a rate of about 1 to about 100 ppm of active ingredient.

The compounds of this invention can be utilized as the sole pesticidal agents or they can be employed in conjunction with other bactericides, fungicides, herbicides, insecticides, acaricides, nematocides and comparable pesticides.

The following examples are presented to illustrate but a few embodiments of the invention and are not to be construed as limiting in scope. All parts and percentages are by weight unless otherwise indicated.

EXAMPLE 1

N-Methanesulfonyl N,N'-dimethyl S-(1-methylpropyl) phosphorodiamidothioate

Sodium hydride (0.6 g., 0.024 mole) and methyl methanesulfonamide (2.7 g., 0.025 mole) were stirred in 20 ml. of tetrahydrofuran (THF) at room temperature for about 24 hours to produce the sodium salt of methyl methanesulfonamide. A solution of S-(1-methylpropyl) phosphorodichloridothioate (5 g., 0.024 mole) in 20 ml. of THF was added all at once to the reaction product mixture from above, and the resulting mixture was stirred 4 hours at ambient temperature to produce N-methanesulfonyl N-methyl S-(1-methylpropyl) phosphoroamidochloridothioate. A solution of methylamine (1.55 g., 0.05 mole) in 10 ml. of THF was added to the reaction product mixture from above, and the resulting mixture was stirred 2 hours at ambient temperature, diluted with 250 ml. of ether, filtered through supercel and evaporated to afford 6.1 g. of product as a brown oil.

The following compounds were prepared by following substantially the procedure set forth in Example 1.

EXAMPLE 2

N,N'-Dimethyl N-(4-Methylphenylsulfonyl) S-(1-Methylpropyl) Phosphorodiamidothioate

EXAMPLE 3

N-Methanesulfonyl N,N'-Dimethyl S-(1-Methylpropyl) N'-(2-Propenyl) Phosphorodiamidothioate

EXAMPLE 4

N-Ethyl N-Methanesulfonyl N'-Methyl S'-(1-Methylpropyl) Phosphorodiamidothioate

EXAMPLE 5

N-Methanesulfonyl N'-Methyl S-(1-Methylpropyl) N-Methylthioethyl Phosphorodiamidothioate

EXAMPLE 6

N-Methanesulfonyl N'-Methyl S-(1-Methylpropyl) N-(2-Propynyl) Phosphorodiamidothioate

EXAMPLE 7

N,N'-Dimethyl S-(1-Methylpropyl) N-Trifluoromethanesulfonyl Phosphorodiamidothioate

EXAMPLE 8

N-Butanesulfonyl N,N'-Dimethyl S-(1-Methylpropyl) Phosphorodiamidothioate

EXAMPLE 9

N-Methanesulfonyl N-Methyl S-(1-Methylpropyl) Phosphorodiamidothioate

EXAMPLE 10

N,N'-Dimethyl S-(1-Methylpropyl) N-Phenylsulfonyl Phosphorodiamidothioate

EXAMPLE 11

N-Ethanesulfonyl N,N'-Dimethyl S-(1-Methylethyl) Phosphorodiamidothioate

EXAMPLE 12

N,N'-Dimethyl S-(1-Methylpropyl) N-(4-Nitrophenyl)sulfonyl Phosphorodiamidothioate

EXAMPLE 13

N-Methanesulfonyl N,N'-Dimethyl S-(1-Methylpropyl) N-(2-Propenyl) Phosphorodiamidothioate

EXAMPLE 14

N'-Ethyl N-Methanesulfonyl N-Methyl S-(1-Methylpropyl) Phosphorodiamidothioate

EXAMPLE 15

N-Methanesulfonyl N'-Methyl S-(1-Methylpropyl) N-Phenyl Phosphorodiamidothioate

EXAMPLE 16

N-Benzyl N-Methanesulfonyl N'-Methyl S-(1-Methylpropyl) Phosphorodiamidothioate

EXAMPLE 17

N-Methanesulfonyl N-(2-Methoxyethyl) N'-Methyl S-(1-Methylpropyl) Phosphorodiamidothioate

EXAMPLE 18

N-Cyclohexyl N-Methanesulfonyl N'-Methyl S-(1-Methylpropyl) Phosphorodiamidothioate

EXAMPLE 19

N,N'-Dimethyl N-(1-Methylethylsulfonyl) S-(1-Methylpropyl) Phosphorodiamidothioate

EXAMPLE 20

N-(4-Methoxyphenyl)sulfonyl N,N'-Dimethyl S-(1-Methylpropyl) Phosphorodiamidothioate

EXAMPLE 21

N-Methanesulfonyl N,N'-Dimethyl S-(1-Methylpropyl) N-Methylthiomethyl Phosphorodiamidothioate Table I below lists the Examples, 1-21, and sets forth the substituents corresponding to the designations, X, $R^1$, $R^2$, $R^3$, $R^4$, and $R^5$ in the structural formula I.

The analytical data, namely, elemental analysis data and nuclear magnetic resonance data, for the examples are set forth in Tables II and III, respectively, below.

TABLE I

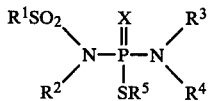

| Ex. No. | X | $R^1$ | $R^2$ | $R^3$ | $R^4$ | $R^5$ |
|---|---|---|---|---|---|---|
| 1 | O | —CH$_3$ | —CH$_3$ | CH$_3$ | H | —CH(CH$_3$)CH$_2$CH$_3$ (1-Methylpropyl) |
| 2 | O | 4-CH$_3$—C$_6$H$_4$— | —CH$_3$ | CH$_3$ | H | —CH(CH$_3$)CH$_2$CH$_3$ |

TABLE I-continued

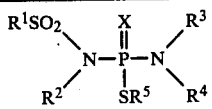

| Ex. No. | X | R¹ | R² | R³ | R⁴ | R⁵ |
|---|---|---|---|---|---|---|
| 3 | O | —CH₃ | —CH₃ | CH₃ | —CH₂CH=CH₂ | —CH(CH₃)CH₂CH₃ |
| 4 | O | —CH₃ | —CH₂CH₃ | CH₃ | H | —CH(CH₃)CH₂CH₃ |
| 5 | O | —CH₃ | CH₃SCH₂CH₂— | CH₃ | H | —CH(CH₃)CH₂CH₃ |
| 6 | O | —CH₃ | —CH₂—C≡CH | CH₃ | H | —CH(CH₃)CH₂CH₃ |
| 7 | O | —CF₃ | —CH₃ | CH₃ | H | —CH(CH₃)CH₂CH₃ |
| 8 | O | —C₄H₉—n | —CH₃ | CH₃ | H | —CH(CH₃)CH₂CH₃ |
| 9 | O | —CH₃ | —CH₃ | H | H | —CH(CH₃)CH₂CH₃ |
| 10 | O | —C₆H₅ | —CH₃ | CH₃ | H | —CH(CH₃)CH₂CH₃ |
| 11 | O | —C₂H₅ | —CH₃ | CH₃ | H | —CH(CH₃)CH₂CH₃ |
| 12 | O | 4-NO₂—C₆H₄— | —CH₃ | CH₃ | H | —CH(CH₃)CH₂CH₃ |
| 13 | O | —CH₃ | —CH₃ | CH₃ | —CH₂CH=CH₂ | —CH(CH₃)CH₂CH₃ |
| 14 | O | —CH₃ | —CH₃ | —C₂H₅ | H | —CH(CH₃)CH₂CH₃ |
| 15 | O | —CH₃ | —C₆H₅ | —CH₃ | H | —CH(CH₃)CH₂CH₃ |
| 16 | O | —CH₃ | —CH₂C₆H₅ | CH₃ | H | —CH(CH₃)CH₂CH₃ |
| 17 | O | —CH₃ | —CH₂CH₂OCH₃ | CH₃ | H | —CH(CH₃)CH₂CH₃ |
| 18 | O | —CH₃ | c-C₆H₁₁— | CH₃ | H | —CH(CH₃)CH₂CH₃ |
| 19 | O | —CH(CH₃)₂ | CH₃ | CH₃ | H | —CH(CH₃)CH₂CH₃ |
| 20 | O | 4-CH₃O—C₆H₄— | CH₃ | CH₃ | H | —CH(CH₃)CH₂CH₃ |
| 21 | O | CH₃ | CH₃ | CH₃ | —CH₂—S—CH₃ | —CH(CH₂)CH₂CH₃ |

TABLE II

Elemental Analyses

| Ex. No. | Emp. Formula | Elemental Analysis Calcd. (Found) | | |
|---|---|---|---|---|
| | | C | H | N |
| 1 | C₇H₁₉N₂O₃PS₂ | 30.65 (30.75) | 6.93 (7.29) | 10.22 (9.96) |
| 2 | C₁₃H₂₃N₂O₃PS₂ | 44.56 (43.25) | 6.61 (6.71) | 8.00 (7.36) |
| 3 | C₁₀H₂₃N₂O₃PS₂ | 38.22 (37.93) | 7.32 (7.53) | 8.92 (8.96) |
| 4 | C₈H₂₁N₂O₃PS₂ | 33.33 (32.93) | 7.29 (7.62) | 9.72 (8.58) |
| 5 | C₉H₂₃N₂O₃PS₃ | 35.76 (33.92) | 7.62 (7.53) | 9.27 (8.25) |
| 6 | C₉H₁₉N₂O₃PS₂ | 36.24 (35.70) | 6.37 (6.30) | 9.39 (9.01) |
| 7 | C₇H₁₆F₃N₂O₃PS₂ | 25.61 (24.80) | 4.88 (4.73) | 8.54 (8.17) |
| 8 | C₁₀H₂₅N₂O₃PS₂ | 42.10 (39.70) | 8.77 (8.12) | 9.82 (7.87) |
| 9 | C₆H₁₇N₂O₃PS₂ | 27.70 (27.64) | 6.54 (6.58) | 10.77 (10.51) |
| 10 | C₁₂H₂₁N₂O₃PS₂ | 42.86 (43.15) | 6.25 (6.34) | 8.33 (8.36) |
| 11 | C₈H₂₁N₂O₃PS₂ | 33.33 (32.97) | 7.29 (7.44) | 9.72 (8.80) |
| 12 | C₁₀H₂₀N₃O₅PS₂ | 37.79 (37.86) | 5.25 (5.41) | 11.02 (11.28) |
| 13 | C₉H₂₁N₂O₃PS₂ | 36.00 (35.59) | 7.00 (7.07) | 9.33 (8.80) |
| 14 | C₈H₂₁N₂O₃PS₂ | 33.33 (32.97) | 7.29 (7.44) | 9.72 (8.80) |
| 15 | C₁₂H₂₁N₂O₃PS₂ | 44.17 (43.93) | 6.44 (6.69) | 8.58 (8.02) |
| 16 | C₁₃H₂₃N₂O₃PS₂ | 44.57 (44.67) | 6.57 (6.62) | 8.00 (7.68) |
| 17 | C₁₀H₂₃N₂O₃PS₂ | 36.36 (34.81) | 6.97 (7.75) | 8.48 (8.82) |
| 18 | C₁₂H₂₇N₂O₃PS₂ | 35.09 (42.20) | 7.89 (7.73) | 8.19 (7.65) |
| 19 | | in test | | |
| 20 | | in test | | |

TABLE III

Numbers are expressed in terms of ppm, δ, relative to the standard, tetramethyl silane (TMS).

Example

1: 3.40 (m, 1H, SCH); 3.10 (d, 3H, NCH₃); 3.08 (s, 3H, CH₃SO₂); 2.72 (m, 1H, NH); 2.72 (d of d, 3H, NHCH₃); 1.65 (m, 2H, SCHCH₂); 1.22 [d, 3H, SCH(CH₃)]; 1.0 (t, 3H, SCHCH₂CH₃).

2: 7.57 (m, 4H, C₆H₅); 3.52 (br s, 1H, NHCH₃); 3.52 (m, 1H, SCH); 3.23 (d, 3H, NCH₃); 3.0 (d of d, 3H, NHCH₃); (s, 3H, 4-CH₃—C₆H₄); 1.88 (m, 2H SCHCH₂); 1.50 [m, 3H, SCH(CH₃)]; 1.0 (t, 3H, SCHCH₂CH₃).

3: 5.52 (m, 3H, CH=CH₂), 3.76 (m, 2H, CH₂CH—CH₂); 3.2 (s, 3H, CH₃SO₂); 3.15 (d, 3H, NCH₃); 2.72 (d, 3H, NHCH₃); 2.70 (m, 2H, SCHCH₂); 1.42 [d, 3H, SCH(CH₃)]; 1.0 (t, 3H, SCHCH₂CH₃).

4: 3.55 (br s, 1H, NHCH₃); 3.55 (m, 1H, SCH); 3.55 (d, 2H, NCH₂CH₃); 3.10 (s, 3H, CH₃SO₂); 2.72 (d, 3H, NHCH₃); 1.64 (m, 2H, SCH₂CH₃); 1.40 [d, 3H SCH(CH₃)]; 1.35 (t, 3H, NCH₂CH₃); 1.0 (t, 3H, SCHCH₂CH₃).

5: 3.67 (br s, 1H, NHCH₃); 3.67 (m, 1H, SCH); 3.67 (m, 2H, NCH₂); 3.23 (s, 3H, CH₃SO₂); 2.8 (m, 2H, NCH₂CH₂); 2.8 (d of d, 3H, NHCH₃); 2.2 (s, 3H, CH₃S); 1.75 (m, 2H,

TABLE III-continued

Numbers are expressed in terms of ppm, δ, relative to the standard, tetramethyl silane (TMS).

Example

SCHCH₂); 1.5 [d, 3H, SCH(CH₃)]; 1.0 (t, 3H, SCHCH₂CH₃).

6: 4.45 (m, 2H, NCH₂); 3.50 (br s, 1H, NHCH₃); 3.50 (m, 1H, SCH); 3.33 (s, 3H, CH₃SO₂); 2.78 (d of d, 3H, NHCH₃); 2.40 (m, 1H, CH₂C=CH); 1.65 (m, 2H, SCHCH₂); 1.47 [d, 3H, SCH(CH₃)]; 1.0 (t, 3H, SCHCH₂CH₃).

7: 3.45 (br s, 1H, NHCH₃); 3.45 (m, 1H, SCH); 3.26 (d, 3H, NCH₃); 2.75 (d of d, 3H, NHCH₃); 1.65 (m, 2H, SCHCH₂); 1.47 [d, 3H, SCH(CH₃)]; 1.0 (t, 3H, SCHCH₂CH₃).

8: 3.35 (br s, 1H, NHCH₃); 3.35 (m, 1H, SCH); 3.35 (m, 2H, SO₂CH₂); 3.18 (d, 3H, NCH₃); 2.65 (d of d, 3H, NHCH₃); 1.62 (m, 4H, SCHCH₂ and SO₂CH₂CH₂); 1.42 [d, 3H, SCH(CH₃)]; 1.0 (t, 3H, SCHCH₂CH₃); 1.0 (m, 2H, SO₂CH₂CH₂CH₂CH₃); 0.95 (t, 3H, SO₂(CH₂)CH₃).

9: 4.25 (br s, 2H, NH₂); 3.40 (m, 1H, SCH); 3.25 (d, 3H, NCH₃); 3.22 (s, 1H, CH₃SO₂); 1.76 (m, 2H, SCHCH₂); 1.50 [d, 3H, SCH(CH₃)]; 1.01 (t, 3H, SCHCH₂CH₃).

10: 7.85 (m, 5H, C₆H₅); 3.67 (br s, 1H, NHCH₃); 3.35 (m, 1H, SCH); 3.15 (d, 3H, NCH₃); 2.70 (m, 3H, NHCH₃); 1.65 (m, 2H, SCHCH₂); 1.50 [d, 3H, SCH(CH₃)]; 1.01 (t, 3H, SCHCH₂CH₃).

11: 3.75 (br s, 1H, NH); 3.40 (m, 1H, SCH); 3.40 (m, 2H, SO₂CH₂); 3.22 (d, 3H, NCH₃); 2.75 (m, 3H, NHCH₃); 1.68 (m, 2H, SCHCH₂); 1.42 [d, 3H, SCH(CH₃)]; 1.40 (t, 3H, SO₂CH₂CH₃); 1.00 (t, 3H, SCHCH₂CH₃).

12: 8.5(q, 4H, C₆H₄); 3.70 (br s, 1H, NHCH₃); 3.50 (s, 1H, SCH); 3.25 (d, 3H, NCH₃); 2.78 (m, 3H, NHCH₃); 1.70 (m, 2H, SCHCH₂); 1.40 [m, 3H, SCH(CH₃)]; 1.00 (t, 3H, SCHCH₂CH₃).

13: 6.02 (m, 1H, NCH₂CH=CH₂); 5.40 (m, 2H, NCH₂CH=CH₂); 4.25 (m, 2H, NCH₂CH=CH₂); 3.25 (s, 3H, CH₃SO₂); 2.80 (m, 3H, NHCH₃); 1.65 (m, 2H, SCHCH₂); 1.40 (d, 3H, SCHCH₃); 100, (t, 3H, SCHCH₂CH₃).

14: 3.50 (br s, 1H, NHCH₃); 3.50 (m, 1H, SCH); 3.30 (d, 3H, NCH₃); 3.25 (s, 1H, CH₃SO₂); 2.92 (m, 2H, NHCH₂); 1.62 (m, 2H, SCHCH₂); 1,40 [d, 3H, SCH(CH₃)]; 1.22 (t, 3H, NHCH₂CH₃); 1.00 (t, 3H, SCHCH₂CH₃).

15: 7.58 (s, 5H, C₆H₅); 3.50 (br s, 1H, NHCH₃); 3.50 (m, 1H, SCH); 3.32 (s, 1H, CH₃SO₂); 2.78 (m, 3H, NHCH₃); 1.70 (m, 2H, SCHCH₂); 1.45 [d, 3H, SCH(CH₃)]; 1.00 (t, 3H, SCHCH₂CH₃).

16: 7.40 (m, 5H, C₆H₅); 4.80 (d, 2H, CH₂); 3.50 (br S, 1H, NHCH₃); 3.50 (m, 1H, SCH); 2.75 (s, 3H, CH₃SO₂); 2.65 (m, 3H, NHCH₃); 1.62 (m, 2H, SCHCH₂); 1.40 [d, 3H, SCH(CH₃)]; 1.00 (t, 3H, SCHCH₂CH₃).

17: 3.90 (m, 4H, NCH₂CH₂); 3.50 (br S, 1H, NHCH₃); 3.50 (m, 1H, SCH); 3.42 (s, 3H, CH₃O); 3.35 (s, 3H, CH₃SO₂); 2.78 (m, 3H, NHCH₃); 1.62 (m, 2H, SCHCH₂); 1.40 [d, 3H,

TABLE III-continued

Numbers are expressed in terms of ppm, δ, relative to the standard, tetramethyl silane (TMS).

Example

SCH(CH₃)]; 1.00 (t, 3H, SCHCH₂CH₃).
18: 4.1 [m, 1H, N—CH(CH₂)₅]; 3.50 (br S, 1H, NHCH₃); 3.50 (m, SCH); 3.18 (s, 3H, CH₃SO₂); 2.75 (m, 3H, NHCH₃); 1.62 (m, 2H, SCHCH₂); 1.62 (m, 2H, SCHCH₂); 1.50 [br m, 10H, (CH₂)₅]; 1.40 [d, 3H, SCH(CH₃)]; 1.00 (t, 3H, SCHCH₂CH₃).
19: 4.20 Im, 1H, OCH); 3.50 (br S, 1H, NHCH₃); 3.50 (m, 1H, SCH); 3.22 (d, 3H, NCH₃); 2.78 (m, 3H, NHCH₃); 1.65 (m, 2H, SCHCH₂); 1.42 [d, 6H, OCH(CH₃)₂]; 1.42 [d, 3H, SCH(CH₃)]; 1.00 It, 3H, SCHCH₂CH₃).
20: 7.65 (m, 4H, C₆H₄); 4.00 (s, 3H, CH₃O); 3.50 (br S, 1H, NHCH₃); 3.50 (m, 1H, SCH); 3.18 (d, 3H, NCH₃); 2.80 (m, 3H, NHCH₃); 1.70 (m, 2H, SCHCH₂); 1.40 [m, 3H, SCH(CH₃)]; 1.00 (t, 3H, SCHCH₂CH₃).

Biological Section

Initial evaluations were made on the following mite, insect, and nematode:

| Code Symbol | Common Name | Latin Name |
|---|---|---|
| TSM | Two-spotted spider mite | *Tetranychus urticae* |
| SAW | Southern armyworm | *Spodoptera eridania* |
| nema | Southern root-knot nematode | *Meloidogyne incognita* |

A test solution containing 600 ppm of test compound was made by dissolving the test compound in a solvent (acetone:methanol, 1:1), adding surfactant and then water to give an acetone:methanol:water system of 10:10:80. A 1:1 mixture of an alkylarylpolyetheralcohol (commercially available under the trademark Triton X-155) and a modified phthalic glycerol alkyl resin (commercially available under the trademark Triton B-1956) were utilized at the equivalent of one ounce per 100 gallons of test solution and a surfactant.

For the mite test, infested bean (*Phaseolus limeanus*) leaf discs (1.25 inches in diameter) containing about 50 mites were placed in a Petri dish lid on a moistened piece of cotton. The leaves were then sprayed with the test solution using a rotating turntable. They were held for 24 hours and then the percent kill was determined.

For the armyworm test, detached bean leaves on pieces of moistened filter paper were sprayed as above for the mite test in similar dishes and allowed to dry. The dishes were infested with 10 third instar southern armyworm larvae. The dishes were covered. After holding for 48 hours, the percent kill was obtained.

For the nematode test, soil was homogeneously inoculated with a macerated blend of tomato roots heavily knotted with the root knot nematode. Ten milliliters of the test soil were added to 200 milliliters of the inoculated soil in a 16 oz. jar to give a concentration by volume of about 30 ppm. The jar was then shaken to insure thorough mixing, immediately uncapped, and allowed to air for 24 hours. The soil was then placed into a 3 inch plastic pot after which time 3 cucumber (*Cucumis sativus*) seeds were planted. About 23 days thereafter, the cucumber plants were removed from the soil and the root system examined for the presence of knots. A total of 15 knots or less was considered a measure of control.

Table IV gives the results of the foregoing biological evaluations.

TABLE IV

| Ex. No. | Biological Evaluation Results | | Nema* |
|---|---|---|---|
| | Two-Spotted Mite | Southern Armyworm | |
| 1 | 100 | 100 | + |
| 2 | 100 | 100 | + |
| 3 | 100 | 100 | + |
| 4 | 100 | 100 | + |
| 5 | 100 | 100 | + |
| 6 | 100 | 100 | + |
| 7 | 100 | 100 | + |
| 8 | 100 | 100 | + |

*+ means control, 15 knots or less, at 150 ppm.

What is claimed is:
1. A compound having the formula:

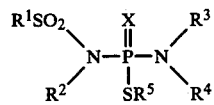

$R^1$ is unsubstituted or substituted $C_1$–$C_6$ alkyl wherein the substituent can be from one to three of the same or different halogens selected from Cl, Br, or F groups;

$C_3$–$C_8$ cycloalkyl;

unsubstituted or substituted phenyl or naphthyl, or can be one to three of the same or different substituents selected from cyano, nitro, halo, alkyl, alkoxy, alkylthio, alkylsulfinyl, alkylsulfonyl, phenoxy, haloalkyl, mono- or di-alkylamino, mono- or di-alkylaminocarbonyl, alkoxy-carbonyl, alkylcarbonyl, alkylcarbonyloxy, phenylthio, phenylsulfinyl, phenylsulfonyl, benzyl, phenylcarbonyl, phenoxycarbonyl, phenylcarbonyloxy, phenylaminocarbonyl, alkenyloxycarbonyl, alkenylcarbonyloxy, aminocarbonyl, or alkylcarbonylamino and the like wherein the alkyl moiety thereof is a straight or branched chain group containing one to six carbon atoms;

$R^2$ is hydrogen;

unsubstituted or substituted $C_1$–$C_6$ alkyl wherein the substituent can be a halo, cyano, alkoxy, alkylthio, alkylcarbonyl, alkoxy-carbonyl, alkoxycarbonyloxy, mono- or di-alkylamino, phenoxy or phenylthio groups;

$C_3$–$C_8$ cycloalkyl;

$C_3$–$C_6$ alkenyl;

unsubstituted or substituted phenyl or naphthyl, or unsubstituted or substituted phenyl($C_1$–$C_5$)alkyl, wherein the substituent on the phenyl or naphthyl ring can be one to three of the same or different substituents selected from cyano, nitro, halo, alkyl, alkoxy, alkylthio, alkylsulfinyl, alkylsulfonyl, phenoxy, haloalkyl, mono- or di-alkylamino, mono- or di-alkylaminocarbonyl, alkoxycarbonyl, alkylcarbonyl, alkylcarbonyloxy, phenylthio, phenylsulfinyl, phenylsulfonyl, benzyl, phenylcarbonyl, phenoxycarbonyl, phenylcarbonyloxyl, phenylaminocarbonyl, alkenyloxycarbonyl, alkenylcabonyloxy, aminocarbonyl, or alkylcarbonylamino and the like wherein the alkyl moiety thereof is a straight or branched chain group containing one to six carbon atoms;

$C_3$–$C_6$ alkynyl;

$R^3$ is hydrogen, methyl or ethyl;

$R^4$ is hydrogen, methyl, $C_1$–$C_6$ alkylthio($C_1$–$C_2$)alkyl, $C_1$–$C_6$ alkoxy($C_1$–$C_2$)alkyl, $C_3$–$C_4$ alkenyl, $C_3$–$C_4$ alkynyl;

$R^5$ is $C_2$–$C_6$ alkyl; and

X is O or S.

2. A compound according to claim 1 wherein X is O.

3. A compound according to claim 2 wherein $R^1$ is an unsubstituted or substituted $C_1$–$C_6$ alkyl group wherein the substituent can be from one to three of the same or different halogens selected from chloro, bromo or fluoro groups;

$R^2$ is an unsubstituted or substituted $C_1$–$C_6$ alkyl group wherein the substituent can be a cyano, alkoxy, alkylthio, alkylcarbonyl, alkoxycarbonyl, alkylcarbonyloxy, mono- or di-alkylamino, phenoxy or phenylthio group;

a $C_3$–$C_6$ alkenyl group; or a $C_3$–$C_6$ alkynyl group;

$R^3$ is a methyl group;

$R^4$ is hydrogen, methyl, $C_3$–$C_4$ alkenyl;

$C_3$–$C_4$ alkynyl;

$R^5$ is $C_2$–$C_6$ alkyl; and

X is O.

4. A compound according to claim 3 wherein $R^1$ is an unsubstituted or substituted $C_1$–$C_6$ alkyl group wherein the substituent can be one to three of the same or different halogens selected from chloro, bromo or fluoro groups;

$R^2$ is an unsubstituted $C_1$–$C_3$ alkyl group;

a $C_3$-alkenyl group; or a $C_3$-alkynyl group;

$R^3$ is methyl;

$R^4$ is hydrogen;

$R^5$ is 1-methylpropyl; and

X is O.

5. A compound according to claim 4 wherein $R^1$ is methyl; $R^2$ is methyl; $R^3$ is methyl; $R^4$ is hydrogen; and $R^5$ is 1-methylpropyl.

6. A compound according to claim 4 wherein $R^1$ is 4-methyl-phenyl; $R^2$ is methyl; $R^3$ is methyl; $R^4$ is hydrogen; and $R^5$ is 1-methylpropyl.

7. A compound according to claim 3 wherein $R^1$ is methyl; $R^2$ is methyl; $R^3$ is methyl; $R^4$ is 2-propenyl; and $R^5$ is 1-methylpropyl.

8. A compound according to claim 4 wherein $R^1$ is methyl; $R^2$ is ethyl; $R^3$ is methyl; $R^4$ is hydrogen; and $R^5$ is 1-methylpropyl.

9. A compound according to claim 4 wherein $R^1$ is methyl; $R^2$ is methylthioethyl; $R^3$ is methyl; $R^4$ is hydrogen; and $R^5$ is 1-methylpropyl.

10. A compound according to claim 4 wherein $R^1$ is methyl; $R^2$ is 2-propynyl; $R^3$ is methyl; $R^4$ is hydrogen; and $R^5$ is 1-methylpropyl.

11. A compound according to claim 4 wherein $R^1$ is trifluoromethyl; $R^2$ is methyl; $R^3$ is methyl; $R^4$ is hydrogen; and $R^5$ is 1-methylpropyl.

12. A compound according to claim 4 wherein $R^1$ is n-butyl; $R^2$ is methyl; $R^3$ is methyl; $R^4$ is hydrogen; and $R^5$ is 1-methylpropyl.

13. A method of controlling pests comprising contacting the pests with a pesticidally effective amount of a compound according to claim 1.

14. A method of controlling pests comprising contacting the pests with a pesticidally effective amount of a compound according to claim 4.

15. A pesticidal composition comprising a pesticidally effective amount of a compound according to claim 1 and an agronomically acceptable carrier.

16. A pesticidal composition comprising a pesticidally effective amount of a compound according to claim 4 and an agronomically effective carrier.

* * * * *